United States Patent [19]

Zartman

[11] Patent Number: 4,651,137
[45] Date of Patent: Mar. 17, 1987

[54] INTRAVAGINAL PARTURITION ALARM AND METHOD FOR USE

[75] Inventor: David L. Zartman, Worthington, Ohio

[73] Assignee: New Mexico State University Foundation, Las Cruces, N. Mex.

[21] Appl. No.: 667,204

[22] Filed: Nov. 1, 1984

[51] Int. Cl.⁴ ............................................. G08B 23/00
[52] U.S. Cl. .................................... 340/573; 128/775; 128/736
[58] Field of Search ................. 340/573; 128/736, 738, 128/361, 775

[56] References Cited

U.S. PATENT DOCUMENTS

| | | | |
|---|---|---|---|
| 3,583,389 | 6/1971 | Harvey | 128/736 |
| 3,781,837 | 12/1973 | Anderson et al. | 128/736 |
| 3,811,423 | 5/1974 | Dickinson, III et al. | 128/738 |
| 3,893,111 | 7/1975 | Cotter | 434/6.5 R |
| 4,028,687 | 6/1977 | Hamaguchi et al. | 340/870.16 |
| 4,031,365 | 6/1977 | Raggiotti et al. | 235/151.3 |
| 4,188,304 | 4/1979 | Mull | 128/2 R |
| 4,312,360 | 1/1982 | Conway et al. | 128/736 |
| 4,377,157 | 3/1983 | Zartman | 128/1 R |
| 4,387,724 | 6/1983 | Zartman | 128/736 |
| 4,396,020 | 8/1983 | Wolff et al. | 128/738 |

OTHER PUBLICATIONS

"An Automatic System for the Measurement and Recording of Basal Temperature in the Human Female", *Fertility and Sterility*, 15: 44–51, (1964), Alvin Singer, M.D. et al.

"Continuously Telemetered Vaginal Temperature in the Baboon", *The Baboon in Medical Research, II*, Ea. H. Vagtborg, University of Texas Press, Austin, pp. 19–35 (1967), A. G. Hendrickx, Ph.D. et al.

"The Detection of Ovulation by Intravaginal Telemetry", *Fertility and Sterility*, vol. 27, No. 9, Sep. 1976, John H. Mattox, M.D. et al.

"Calving Signs You Can Use", *Hoard's Dairyman*, 101:1188, 1956, by Melvin Scholl.

"Heat-Tolerance Studies of Fat-Tailed Sheep in the Subtropics", *J. Agri. Sci.* (Camb.) 47:280–286, 1956, Hafez et al.

"Vaginal Temperature of Dairy Cows Before and After Calving", *JAVMA* 131 ;381–383 (1957), I. D. Porterfield, Ph.D. et al.

Report of the New York State Veterinary College at Cornell University, 1962–1963, S. J. Roberts reference, p. 93.

"Predicting the Time of Parturition in the Normal Cow ...", The Veterinary Record, vol. 75, No. 14, by Roger Ewbank.

List Continued on next page.

Primary Examiner—Charles A. Ruehl
Assistant Examiner—Jeffery A. Hofsass
Attorney, Agent, or Firm—Lane & Aitken

[57] ABSTRACT

A system for detecting the onset of parturition by a mammalian female comprises an anchor, a temperature sensing means affixed to the anchor, and an alarm means, wherein the anchor has a diameter that is smaller than an interior diameter of a posterior portion of the female's vagina at the onset of parturition but greater than the interior diameter prior to the onset of parturition, and smaller than an interior diameter of an anterior portion of the female's vagina before and at the onset of parturition, such diameters being a function of muscular activity, such that the anchor is retained in the anterior portion for a period prior to the onset of parturition and expulsed at the onset of parturition, and wherein the sensing means senses a temperature differential at the location of the anchor before and after expulsion and actuates the alarm means. A method for detecting the onset of parturition, a system and method for predicting the onset of parturition, a system and method for detecting the attainment of fetal parturition readiness, and a system and method for detecting the occurrence of fetal stress syndrome are also described.

23 Claims, 4 Drawing Figures

OTHER PUBLICATIONS

"The Fall in Rectal Temperature Seen Before Parturition in Sheep", *J. Reprod. Fert.* (1969), 19, 569-571, by R. Ewbank.

"Fluctuations in Rectal Temperature of Swine at Parturition", *Canadian Veterinary Journal* 13:72-74 (1972), G. J. King et al.

"Reproduction in the Dog and Cat, " *Reproduction in Domestic Animals*, 3d Ed. Academic Press, NY, p. 665, H. H. Cole, 1977.

"Determinants of Maternal Temperature During Labor", *Am. Jour. Obstet. Gynec.* 143:97-103 (1982), R. C. Goodlin et al.

"Variations in Body Temperature in the Late Stage of Pregnancy and Parturition in Bitches", *Jpn. J. Vet. Sci.* 44(4), 571-576 (1982), T. Tsutsui.

"The Temperature Phenomenon Before Parturition and Its Clinical Importance", JAVMA, 102 (Feb.): 123, 1943 by Leo Weisz, D.v.m.

"Reproductive Characteristics of Holstein Heifers Fitted with Intravaginal Temperature Transmitters", *Dpt. of Animal and Range Sci. and Exptal Stats.*, New Mexico St. Univ., 1983, vol. 19, No. 4, pp. 541-554 by D. L. Zartman.

K. Maatje and W. Rossing, "Detecting Oestrus by Measuring Milk Temperatures of Dairy Cows During Milking," (from *Livestock Production Science*) 1975, from The Netherlands, pp. 85 to 89.

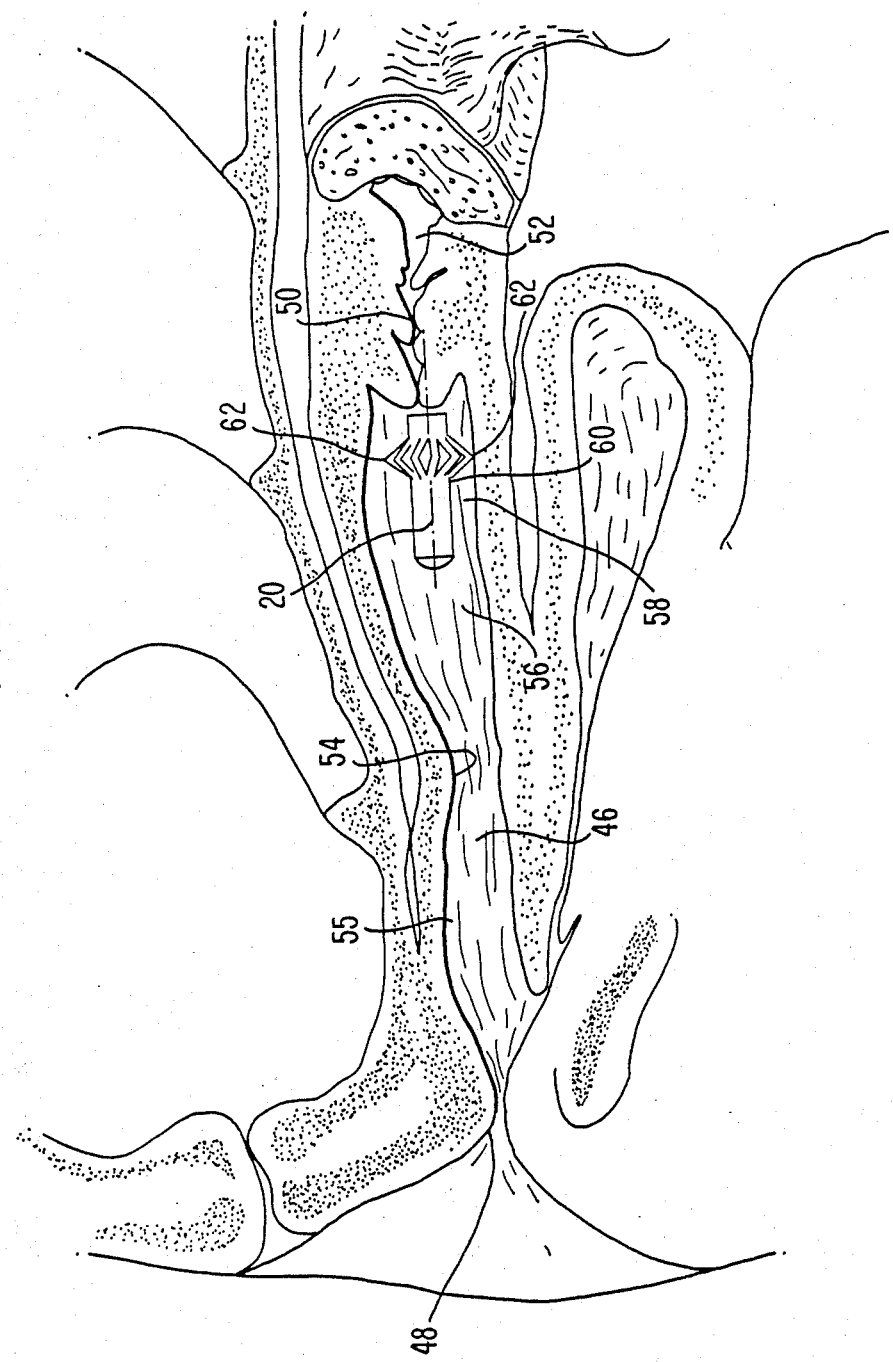

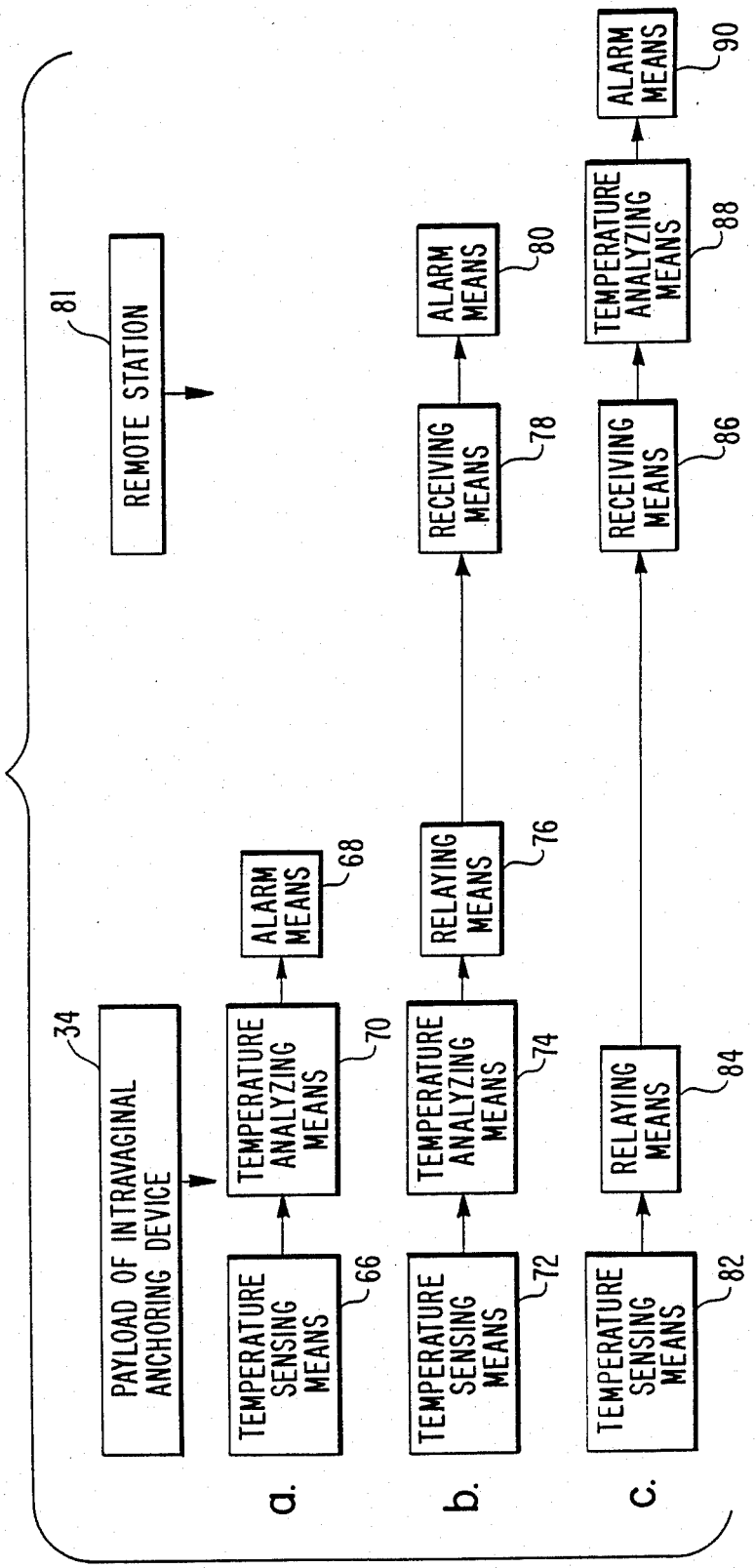

INTRAVAGINAL PARTURITION ALARM AND METHOD FOR USE

BACKGROUND OF THE INVENTION

1. Introduction

This invention pertains to an intravaginal alarm for predicting and detecting parturition and detecting the related events of fetal readiness and fetal stress syndrome in mammalian animals. The invention also pertains to methods for detecting these events.

2. Description of the Prior Art

The inability to detect the onset of parturition has proved to be a dilemma to both humans and animal husbandmen. It is not uncommon for women to unexpectedly give birth before arriving at a medical facility, and the occurrence of false labor, and the inconveniences related thereto, are commonplace. The problems are even greater for the animal husbandman, who must attempt to determine the onset of parturition without the aid of intelligent input from the animal herself. For the animal husbandman, it is also difficult to detect the onset of parturition by an animal unless the animal is under constant surveillance.

Researchers in the past have noted subtle changes in activity and appearance of an expectant female within about two weeks of parturition but these subtleties are not universal among animals of the same species nor are they necessarily similar from one species to the next. Numerous attempts at detecting the onset of parturition by noting such subtleties have accordingly failed. Exemplary of such failures is a study reported by R. Ewbank entitled "Predicting the Time of Parturition In the Normal Cow: A Study of the Pre-Calving Drop in Body Temperature in Relation to the External Signs of Imminent Calving,", presented at *Vet. Rec.* 75:367–371 (1963), in which the monitoring of subtle changes in 21 female cows led the researchers to believe that nine of the cows, which calved within two to twelve hours, were not expected to calve and six other cows, which failed to calve within the succeeding twelve hours, were expected to undergo imminent parturition.

As a result of the failure of the livestock industry to establish a suitable test regimen for the determination of the onset of parturition by changes in activity and appearance of the female, direct 24-hour observation by farm personnel has typically been the only dependable means of insuring that an expectant female receive appropriate assistance at the time of delivery. As stated by one writer, "While it is possible to predict the time of calving within a day or so, advanced prediction of calving time to within an hour or so is impossible. As a result, repeated checking of animals known to be near parturition is one of the only ways to determine the exact time of birth. This can be a timeconsuming process and it runs the risk that not only may the birth occur undetected, but also that the farmer may become involved too early and cause injury to the cow or calf by rushing the process." Scott et al, "Electronic Developments in Dairy Herd Management," *Proc. of the Symp. Automation in Dairying, Wageningen, the Netherlands*, pp. 221–236 (1983). Regarding sows, another writer commented, "Because farrowings in the normal way do occur at all hours of the night and day and gestation periods can vary in length from one sow to the next by several days, precise scheduling of personnel for supervision can be costly and difficult and perhaps even impossible to arrange unless the time of parturition can be closely controlled." Gordon, *Controlled Breeding in Farm Animals*, copyright 1983 by Pergamon Press, New York, N.Y. p. 333.

Despite the admonitions of writers in the art that, when the onset of parturition is to be detected by direct observation, monitoring personnel be available at all hours of the day, budgetary concerns and practical difficulties have caused many farm managers who rely on direct observation techniques to provide only partial monitoring of the expectant females. The result is a high mortality rate for the offspring. In the New Mexico State University dairy herd, nearly 10 percent of the calves are listed as dean-on-arrival, a statistic almost completely due to nighttime births which are unattended. Other researchers have found that the mortality rate for calves involved in difficult births is four times higher than for those born without difficulty and that, of calves dead at birth, approximately 90 percent of the losses are attributable to delays in receiving assistance or the amount of difficulty and time required to remove the calf. Laster et al, "Factors Influencing Peri-and Early Post-Natal Calf Mortality," *J. Anim. Sci.* 37:1092–1097 (1973). Another writer reports that cattle experience dystocia (difficult birth) in 30 to 60 percent of births in primiparous dams, in 8 to 25 percent of second calf births, and in 2 to 8 percent of births to mature dams, and that as many as 70 percent of the calves lost at parturition have functional lungs, indicating that they were not stillborn but rather died as a result of injuries and physiologic trauma during prolonged and difficult delivery, problems that could normally have been overcome if monitoring personnel had been present. Hafez, *Reproduction in Farm Animals*, Fourth Edition, copyright 1980 by Lea and Febiger, Philadelphia, Penna. p. 340.

Losses resulting from the failure to provide constant monitoring, when direct observation is the only means of detecting the onset of parturition, are not limited to the cattle industry. In a study involving more than 150 supervised farrowings, the loss of all piglets from birth to weaning was reduced to less than six percent during a period of close supervision, in contrast to a loss of more than 20 percent in the same herd before and after the period of supervision. Dziuk, "Control and Mechanics of Parturition In the Pig," *Anim. Reprod. Sci.*, 2:335–342 (1979). Other research has demonstrated that resuscitation of a substantial proportion of apparently dead piglets is possible. Milosavljevic et al, "The Revival of Apparently Stillborn Piglets," *Acta. Vet. Beograd.*, 22:71–76 (1972). Without close supervision, it has been estimated that losses in the United States alone of piglets near birth is about 22,000,000 annually, a figure that exceeds death loss from transmissible gastroenteritis, the dramatic killer of piglets, by about 19 times, and exceeds by a factor of several times all other death losses from disease and management combined. Dziuk, supra. With regard to horses, it has been found that 83.6 percent of horse foalings occurred at night with the great majority coming within two hours before or after midnight, such that the failure to monitor expectant mothers during this period can result in death or serious complications. Finally, even though human females have attempted to counteract the problem by obtaining professional advice on a frequent basis and by reporting to a hospital at the first sign of parturition, many false starts and emergency runs occur due to the inadequacy of reliance upon subjectively observable changes.

Others in the prior art have appreciated the inadequacy of directly monitoring changes in expectant farm animals to determine the onset of parturition and, accordingly, a number of devices have been suggested for making the determination. The devices generally attempt to determine the onset of parturition by automatically detecting bodily conditions commonly associated therewith. Thus, devices have been developed for detecting tail raising in cows and horses, lying prone in horses, increased heart rate in horses, and fetal water bag swelling in sheep. The devices are unsatisfactory because, inter alia, they are subject to false alarms, they are limited to a particular family or families of animals, and/or they require considerable maintenance. Also, in the case of the device used to detect fetal water bag swelling in sheep, which involves the precise intravaginal insertion of a thermister probe that senses a temperature difference upon explusion, the device is incapable of being retained by the animal for extended periods of time, causes an increased liklihood of infection and infestation by screw worm larvae, and causes stress and discomfort. Finger et al, Erste Mitteilung uber Entwicklung und Einsatz eines elktronischen Geburtswachters fur Schafe, *Berl. Munch. Tierarztl. Wschr.*, 95:130–132 (1982).

The devices disclosed in U.S. Pat. No. 3,583,389, issued to Harvey, and U.S. Pat. No. 4,028,687, issued to Hamaguchi are similar to the intravaginal parturition device for sheep, disclosed in the Finger reference, supra, in that they are designed to be inserted into an animal's vagina and expulsed at parturition, whereupon a signal is generated. In the Harvey patent, an egg-shaped device is disclosed that is particularly adapted for use in sows. The device is provided with a transmitter that is energized or deenergized in response to the attainment of a predetermined temperature. Upon expulsion of the device from the vaginal cavity, the transmitter is activated to transmit a signal that in turn activates a warning system such as an audible sound or a light. In the Hamaguchi et al reference, the device is similarily actuated upon expulsion from the vaginal cavity, but the actuation is in the form of the generation of an electric current that is shorted out while the device is located intravaginally. Like the Harvey invention, that of the Hamaguchi et al device is generally egg-shaped but, in one form, is provided with an elastic annular projection to assist in the retention of the device within the vagina. While in some respects the Harvey and Hamaguchi et al inventions may be improvements over the prior art, they do not provide a complete solution to the problem.

Aside from the use of the temperature change upon explusion of an object from a reproductive tract as an indicator of parturition, others have attempted without success to show a reliable relationship between temperature phenomena and the onset of parturition and related events. Eight research reports have been summarized as describing a body temperature increase during the latter part of pregnancy with a substantial drop during the last few days to a few hours before parturition. Ewbank, *Vet.Rec.* 75:367–371, supra. A brief mention of a temperature drop in dogs about one day before parturition has more recently been recorded. Cole et al, *Reproduction in Domestic Animals*, Third Edition, copyright 1977 by Academic Press, New York, N.Y. p. 517; Tsutsui et al, "Variations in Body Temperature in the Late Stages of Pregnancy and Parturition in Bitches," *Jpn.J. Vet.Sci.*, 44:571–576 (1982).

However, for a number of reasons, the efforts of workers in the field to develop a reliable relationship between temperature phenomena and the onset of parturition have failed. In fact, the prior art would actually lead one away from the use of temperature measurements as a reliable tool in the forecasting and identification of occurrences related to parturition. Researchers in the field generally reported failures in their attempts to use such measurements in forecasting and determining occurrences related to parturition, thus dissuading other researchers from further study. Additionally, with only one exception, no current textbooks on reproductive or general animal physiology have been found that comment on any temperature phenomenon related to parturition and, furthermore, even the prestigious reference book, *The Merck Veterinary Manual*, Fifth Edition, makes no mention of any species that have a temperature phenomenon associated with parturition.

Closely related to the failure of the prior art to effectively detect the onset of parturition is the failure of the prior art to detect the occurrence of fetal readiness. In order to determine the most optimum time to induce labor in mares, for example, attempts have been made to gauge fetal readiness by criteria that typically include the occurrence of a minimal estimated length of pregnancy (about eleven months, two weeks) and subjective opinions regarding the fullness of the teats, the looseness of the pelvis, and the position of the fetus. Because these criteria only imprecisely indicate an appropriate point at which the induction of labor is safe, there is a substantial risk to the fetus.

The prior art has also failed to satisfactorily determine the occurrence of fetal stress syndrome, which may occur during parturition. When fetal stress syndrome occurs, the fetus' temperature begins to climb dramatically, and the mother's temperature similarly undergoes a marked temperature increase. It is important to administer suitable treatment to remedy the problem as soon as possible in order to reduce the risk of fetal mortality or injury. Weisz, "The Temperature Phenomenon Before Parturition and Its Clinical Importance," J.A.V.M.A., 102:123 (1943). While the prior art has appreciated the importance of suitably administering treatment to the mother and fetus upon the occurrence of fetal stress syndrome, the prior art has failed to adequately provide a means for detecting the onset of fetal stress syndrome, such that the treatment can be immediately applied.

In view of the shortcomings of the prior art, it is an object of the present invention to provide an improved system and method for predicting the onset of parturition in a mammalian female.

It is a further object of the present invention to provide an improved system and method for detecting the onset of parturition in a mammalian female.

It is a further object of the present invention to provide an improved system and method for determining the attainment of fetal readiness for parturition in a mammalian female.

It is a further object of the present invention to provide an improved system and method for determining the occurrence of fetal stress syndrome in a mammalian female.

It is a still further object of the present invention to provide a system and method for predicting the onset of parturition, and determining the occurrences of fetal readiness, the onset of parturition, and fetal stress syndrome, that can be adapted for a number of families of mammalian females with minor modifications and are accurate, reliable, safe, convenient and economical.

Other objectives of the present invention will be apparent from the following detailed description of the preferred embodiments.

SUMMARY OF THE INVENTION

In accordance with the present invention, a system and method for detecting the onset of parturition by a mammalian female is provided. The system includes an anchor, a temperature sensing means affixed to the anchor, and an alarm means. The anchor has a diameter that is smaller than an interior diameter of a posterior portion of the female's vagina at the onset of parturition, but greater than the interior diameter prior to the onset of parturition. The anchor's diameter is also smaller than an interior diameter of an anterior portion of the female's vagina before and at the onset of parturition, such diameters being a function of muscular activity, such that the anchor is retained in the anterior portion for a period prior to parturition and expulsed at the onset of parturition. The sensing means senses a temperature differential at the location of the anchor before and after expulsion and activates the alarm means.

The invention also provides a method for the prediction of the onset of parturition and the detection of the attainment of fetal readiness in the fetus of a mammalian female, including the steps of measuring the intravaginal temperature of the female for a plurality of days at the same time of day for each of the days, averaging the temperatures to determine a standard intravaginal temperature for the female for the particular time, and subsequently measuring an intravaginal temperature for the female for the particular time that is at least about 0.4 degrees Celcius lower than the standard temperature, such that the onset of parturition is predicted and the attainment of fetal readiness in the fetus is detected by the subsequent measurement.

Also in accordance with the present invention, a method for detecting the occurrence of fetal stress syndrome in a mammalian female is provided and involves the steps of measuring the intravaginal temperature of the female for a plurality of days at the same time for each day, averaging the temperatures to determine a standard intravaginal temperature for the female for the particular time and, subsequently, during parturition, measuring a rapidly increasing intravaginal temperature, whereby the occurrence of fetal stress syndrome is detected by the subsequent measurement.

BRIEF DESCRIPTION OF THE DRAWINGS

FIG. 3 is a cross-sectional view of a reproductive tract of a mammalian female, depicting the placement of the device of FIG. 1 therein.

FIG. 4 is a schematic illustration of the system of the present invention.

DESCRIPTION OF THE PREFERRED EMBODIMENTS

The present invention provides a system and method for warning a person of an impending parturition in advance of the onset of parturition, detecting the attainment of fetal readiness, alerting a person to the onset of parturition, alerting a person to fetal stress syndrome during parturition, and identifying the optimum time for the induction of delivery or Caesarean section. The invention is suitable for use with all mammalian females and is especially suitable for humans and animals in the bovine, ovine, caprine, equine and porcine families. The invention involves the placement of a temperature sensitive element, disposed within an anchor, into the vaginal cavity of a mammalian female who is to become or already is pregnant. Temperature measurements made during the period of insertion are used to predict the onset of parturition, determine the occurrence of fetal readiness and fetal stress syndrome, identify the optimum time for inducing delivery or performing Caesarean section and, upon expulsion, a temperature drop is used to detect the onset of parturition.

In order to detect the onset of parturition and related events, an important feature of the present invention is an anchor that is capable of being retained for extended periods of time prior to the onset of parturition, but that is readily expulsed upon the occurrence of the onset of parturition. In accordance with the present invention, the anchor has a diameter that is smaller than an interior diameter of a posterior portion of the female's vagina at the onset of parturition but greater than the interior diameter prior to the onset of parturition. The anchor's diameter is also smaller than an interior diameter of an anterior portion of the female's vagina before and at the onset of parturition, such diameters being a function of muscular activity, such that the anchor is retained in an anterior portion for a period prior to parturition and expulsed at the onset of parturition.

Figure 1:
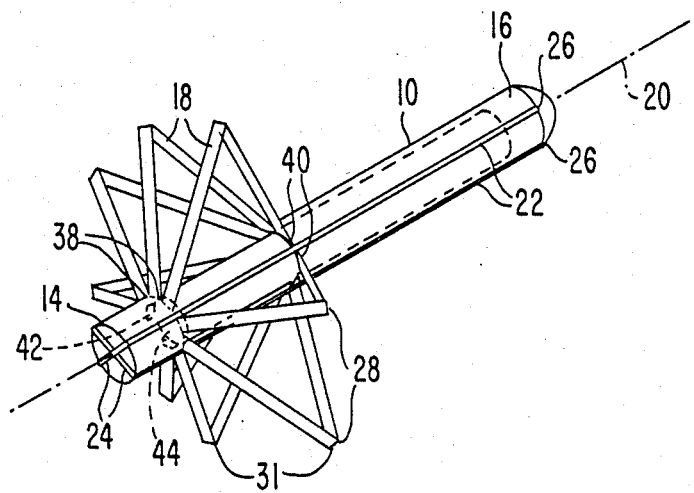
FIG. 1 is a prospective view of a device suitable for use in the practice of the invention.
Figure 2:
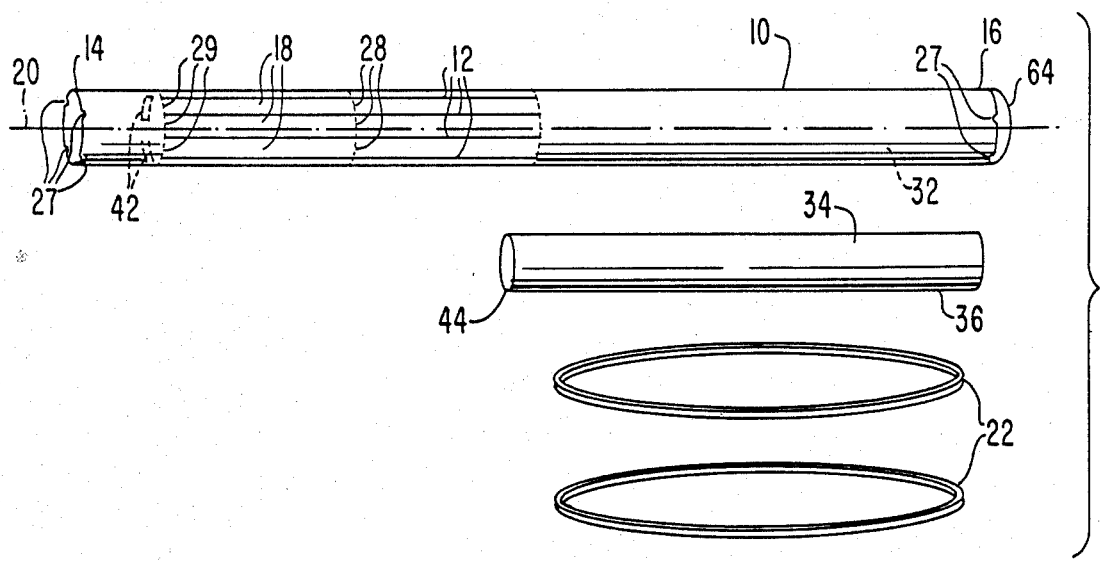
FIG. 2 is a prospective view of unassembled parts of a preferred embodiment of the device depicted in FIG. 1.

An anchor suitable for use in the present invention is depicted in the appended drawings. In the depicted embodiment, an elongated tubular body 10 is provided with a plurality of slots 12 that are disposed substantially parallel to each other and to the length of the body. In an expanded position, a first end 14 and second end 16 of the body are moved towards each other and flange portions 18 of the body that are disposed between adjacent pairs of the slots are distended away from a central axis 20, as depicted in FIG. 1, to form a flanged area. In the collapsed position, as depicted in FIG. 2, the ends 14, 16 of the body are moved away from each other and flange portions 18 are retracted towards axis 20.

In the depicted embodiment, a biasing means 22 is provided in the form of elastic bands to urge the body into the expanded position depicted in FIG. 1. Bands 22 are applied by affixing a first end 24 of the bands to end 14 of the body and a second end 26 of the bands to the other end 16 of the body. Notches 27 are provided to retain bands 22 in position. In this fashion, the bands exert a pressure that urges ends 14, 16 of the body together and, at the same time, urges flange portions 18 outwardly. In another embodiment, the body is constructed in such a fashion to comprise an inherent bias of the body, such that the body naturally assumes the expanded position.

Flange portions 18 are each provided with creases 28, 29, 30 such that, in the expanded position as depicted in FIG. 1, the flange portions are substantially angular in shape, the vertices 31 of the angular shapes being the points most remote from axis 20.

Being of hollow construction, body 10 comprises a cavity 32 adjacent to end 16. Into the cavity is inserted a payload 34 that consists of an instrument package. The instrument package includes a temperature sensing means and may also include a temperature analyzing means, an alarm means and/or a signal relaying means. The payload can be retained within cavity 32 without a separate enclosure, or the payload can be enclosed in a capsule 36 before being inserted into cavity 32. The payload is preferably first enclosed within capsule 36 and sealed, such that the capsule is impervious to fluids found in the vagina. In the event that a capsule 36 is employed, it is retained in cavity 32 by any suitable means, including the use of an adhesive or by rendering the external diameter of capsule 36 slightly larger than the internal diameter of cavity 32, such that capsule 36 exerts a retaining pressure against the walls of cavity 32. If a capsule is not employed, the payload can be directly secured within cavity 32 by similar means.

The intravaginal anchoring device is also provided with a distancing means for maintaining a minimum distance between the end 38, 40 of the flange portions 18 when the device is in the expanded position as depicted in FIG. 1. In the depicted embodiment, the distancing means comprises capsule 36 which acts as a protrusion extending toward end 14 of the body and at least one stop 42 affixed adjacent to ends 38 of flange portions 18. A minimum distance between the ends of the flanges is thereby maintained when end 44 of the capsule rests against stops 42. In another preferred embodiment, the body is constructed in such a fashion as to include an inherent bias, such that the body naturally assumes the configuration depicted in FIG. 1, whereby the minimum distance is substantially maintained without the need of a separate distancing means.

Loop 64 is affixed to an end 16 of the tubular body so that, when inserted, the loop will be disposed posteriorly in the animal's vagina. The loop facilitates the attachment of a hooked retrieval device when the removal of the anchor is desirable. The provision of a loop is not as important when the recipient animal is a large animal since, in such cases, the anchor can be easily retrieved with a gloved hand.

In FIG. 3, the reproductive tract of a cow is depicted prior to the onset of delivery and the positioning of the device is illustrated. In FIG. 3, it is seen that the animal's vagina 46 extends from vulva 48 to cervix 50, which leads to uterus 52. Muscle contractions such as contraction 54 occur within the vagina and it can be seen that posterior portion 55 is generally more tapered than anterior portion 56 prior to the onset of delivery. Deep vagina 58 is located in the anterior portion of the vagina, adjacent to cervix 50. In use, the intravaginal anchoring device 60 is disposed within the vagina in a substantially horizontal position. As will be seen in FIG. 3, the greatest distance between a pair of opposing flange portions 62 is greater than the contracted internal diameter of posterior portion 55 but less than the expanded internal diameter of anterior portion 56, such that both flange portions of an opposing pair of flange portions do not simultaneously exert invasive pressure on interior surfaces of the anterior portion. Thus, the anchoring device does not attach or adhere to the anterior portion at all but is instead free and mobile.

The intravaginal anchoring device 60 is essentially retained by muscular contraction of the vagina, particularly in region 54. Yet, its design is such that peristaltic muscular activity of the vagina is not capable of propelling the device 60 toward and through the posterior portions of the vaginal tract 54 and 55. Only during the act of hard labor and associated relation of the pelvis coupled with coincidental hard contractions of vaginal musculature is the intravaginal anchoring device 60 expelled from the anterior vaginal cavity 58.

The intravaginal anchoring device is designed for non-surgical placement in the vagina of any mammalian female, including humans and farm animals of the bovine, ovine, caprine, equine or porcine families. The size of the anchor is dictated by the size of the vaginal cavity of the female into which the device is being applied, and this size is dependent upon the age and mammalian family of the animal. The size is selected such that (1) the greatest distance between pairs of opposing, extended flange portions is less than the expanded internal diameter of anterior portion 56 but (2) great enough such that the device does not naturally pass out of the vagina, except in the case of the onset of parturition. This latter feature is established by providing that the greatest distance between pairs of opposing flange portions, in the expanded position, is greater than the interior diameter of posterior portion 55 prior to the onset of parturition as depicted in FIG. 3. Posterior portion 55 expands at the onset of parturition and the greatest diameter between pairs of expanded, opposing flange portions is less than the interior diameter of posterior portion 55 at the onset of parturition. Thus, it has been found, for example, that a unit with a tubular body having a length of about 9.5 to 16 cm when compressed and slots of about 4 to 12 cm in length is preferable for cows, heifers and mares, such that the distal vertices of expanded flange portions define a periphery having a diameter of about 6.5 to 9 cm. Such a size has also been used satisfactorily on sows, but units in which the diameter is about 4.5 to 6.5 cm are preferred. A smaller but similarly designed unit is suitable for human females and other small mammals, such as ewes. For humans, a unit having a tubular body the approximate size of a common tampon, with slots of such length that the distal vertices of expanded flange portions define a periphery having a diameter of about 2.5 cm is satisfactory. In any case, a minimum distance between ends 38, 40 of the flange portions in the expanded position is maintained, and a suitable minimum distance has been found to be about 2 cm.

The anchoring device is composed of a biocompatible material, such as nylon or other non-toxic plastic, that is safe and tissue compatible for live animals. Food grade nylon is a particularly preferred material. The materials of which the device is composed are also preferably easily sterilized by gas, chemicals or irradiation without significantly altering the nature or performance of the anchor.

The anchor can be injection molded or molded in tubular stock with subsequent milling to produce slots to allow the expansion from within of the tubular body to produce the flange portions. The slots are preferably very narrow, such that the flange portions are as wide as possible, but wider slots may be suitable for certain applications. As indicated above, the tubular body will preferably be constructed such that the flange portions 18 naturally assume the expanded position depicted in FIG. 1 and, by virtue of the deformability of the plastic material, are deformable to achieve the collapsed position depicted in FIG. 2.

In a preferred embodiment, capsule 36 is composed of a biocompatible material and is releasably retained within cavity 32 by providing that the exterior diameter of the capsule is slightly larger than the interior diameter of the cavity. In this fashion, capsule 36 can be removed from tubular body 10 after a particular application and disposed of, while the tubular body can be used again, or vice versa. In a particular embodiment, disposable plastic syringes, especially those that have a siliconized interior, are used to encapsulate electronic instruments, whereby the ends of the capsule are heat sealed after the instrument package is loaded.

In order to insert the intravaginal anchoring device, the flange portions are retracted and the device is passed through the vulva and into the vagina. In order to facilitate the insertion of the device in its collapsed position, an apparatus and method such as that described in the copending application of David L. Zartman, entitled "Apparatus for Insertion of an Intravaginal Article", filed concurrently herewith and hereby incorporated by reference, is employed. Due to the presence of the biasing means that urges the tubular body into the expanded position, the anchoring device assumes the expanded position after insertion into the vagina. When the prescribed period of retention ends, the anchoring device is removed by a gloved hand in the case of larger mammalian animals, or by the attachment of a hook to loop 64, or by the onset of parturition. Due to the flexibility of flange portions 18, the device can be pulled through an area of muscular contraction 54 without difficulty.

The anchor is described in more detail in the copending application of David L. Zartman, entitled "Intravaginal Anchor," filed concurrently herewith and hereby incorporated by reference.

In order to detect the onset of parturition in accordance with the present invention, a temperature sensing means is affixed to the anchor described above and an alarm means is provided. Temperature sensing means suitable for use in the invention are known in the prior art and are small enough to fit within payload 34. A sensing means is selected that is capable of sensing differences of about 3° celsius between the intravaginal temperature of the mammalian female and the temperature existing in the exterior environment, after the intravaginal device is expulsed ahead of the fetus. Preferably, the sensing means is capable of sensing the difference within about one minute of expulsion. Upon sensing the difference, the sensing means generates a signal which is delivered to the alarm means.

In the embodiment depicted in FIG. 4a, temperature sensing means 66 and alarm means 68 are contained in payload 34, optionally along with a temperature analyzing means 70. Upon expulsion, the sensing means delivers a signal to the alarm means directly or through the analyzing means. The signal is either a positive signal, whereby the sensing means is activated to send a signal upon expulsion, or a negative signal, whereby the sensing means is inactivated to discontinue the transmission of a preexisting signal. In the embodiment depicted in FIG. 4a, the alarm means is perceivable by a farm worker at the location of the animal. The alarm means is thus audibly perceivable, in the form of a siren or the like, or visually perceivable, in the form of a flashing light or a colored substance.

In view of the large range provided many farm animals and the possibility that an audibly or visually perceivable alarm may go undetected, a preferred embodiment as depicted in FIG. 4b. There, temperature sensing means 72 and, optionally, analyzing means 74 are disposed within payload 34 but alarm means 80 is maintained at a remote station 81, such as a farm building. Relaying means 76 is also contained within payload 34 and receiving means 78 is also maintained at remote station 81, such that, upon expulsion, the sensing means delivers its signal, via the relaying and receiving means, to the alarm. The alarm is of any suitable form, such as a bell, siren, light, or a display on a cathode ray tube or more conventional graph. Preferably, the alarm is audibly or visually perceivable to such an intensity that it is unnecessary for a farm worker to constantly monitor the alarm means.

In order to predict the time of the onset of parturition in advance, the provision of a temperature analyzing means is preferred and, since such prediction in accordance with the invention does not require the expulsion of the intravaginal device, the alarm is preferably not located within the payload but rather at a remote station. Thus, suitable embodiments for predicting the time of the onset of parturition are depicted in FIG. 4b, as described above, or FIG. 4c. In the alternative embodiment depicted in FIG. 4c, sensing means 82 and relaying means 84 are contained within payload 34 and receiving means 86, temperature analyzing means 88 and alarm means 90 are maintained at remote station 81.

In accordance with the present invention, the time of the onset of parturition is predicted by precisely measuring temperature changes in the expectant female. Any suitable miniaturized temperature sensing means known in the art that is capable of accurately measuring temperatures within at least tenths of a degree celsius is affixed to an anchoring device and inserted within the anterior portion of the female's vagina. The sensing means generates signals identifying the temperatures sensed and, in the preferred embodiment, these are received and analyzed by the temperature analyzing means. The analyzing means is programmed to recognize a particular set of temperature data as constituting an alarm condition, and at that point generates a signal that is delivered to an alarm means, which is activated thereby.

In order to determine the alarm condition, the intravaginal temperature of the expectant female is first sensed for a plurality of days. Due to diurnal variations in intravaginal temperatures, it is important that the measurements be made at the same time of day each day or that suitable calibrations be made. It is possible to monitor temperatures at more than one time per day, as long as the measurements taken at one time are tracked independently of those taken at another time. The temperature measurements for a given time are then averaged to provide a standard intravaginal temperature that is peculiar to the particular animal being monitored. The number of days that the measurements are taken is any number that will produce a statistically reliable standard temperature. In a preferred embodiment, the number of days is five.

Once the standard temperature has been determined, the system is prepared to sense deviations from the standard that signify that a certain number of days remain until the onset of parturition. Thus, when a subsequent temperature, which is measured at the same time of day as the temperatures that are used to compute the standard, is sensed that is at least about 0.4° celsius, and preferably within the range of 0.4° to 1.0°, celsius, lower than the standard temperature, it can be predicted that the onset of parturition will occur within six days and probably within three days.

To further ensure the accuracy of prediction, another deviant temperature is preferably sensed after the standard temperature has been determined but before the above-mentioned lower temperature is sensed. This other deviant temperature, which is measured at the same time of day as the temperatures that are used to compute the standard, is at least about 0.2° celsius, and preferably within the range of about 0.2° to 0.5° celsius, higher than the standard temperature, and occurs not more than about three days before the above-mentioned lower temperature.

Without intending to limit the scope of the invention in any way, it is hypothesized that the occurrence of the lower temperature is about 0.4° to about 1.0° celsius is related to the fetus' full attainment of respiratory capacity. The use of this range is suitable for predicting in advance the occurrence of the onset of parturition in mammals of the human species and bovine, orine, caprine and porcine families, and is especially suitable for predicting in advance the occurrence of the onset of parturition in mammals of the equine family. Similarly, the range of the higher temperature and the temporal relationships of the occurrences of the deviant temperature and the onset of parturition as described above, are suitable for use in making predictions for mammals of the human species and bovine, ovine, caprine and porcine families, and are especially suitable for use in making predictions in the case of mammals of the equine family.

In accordance with another embodiment of the present invention, the attainment of parturition readiness of the fetus, including the fetus' attainment of lung function, is identified concurrently with the measurement of the lower temperature referred to above. By determining the standard intravaginal temperature and sensing the lower temperature, preferably in conjunction with the earlier sensing of the above-mentioned higher temperature, the farm worker can effectively determine the point in time when the fetus is capable of living normally outside of the womb. This determination allows the delivery to be expedited by the administration of drugs or by Caesarian section without jeopardizing the newborn's health.

In still another embodiment of the present invention, the occurrence of fetal stress syndrome is effectively identified. Fetal stress syndrome occurs immediately before parturition and typically is due to inadequate pelvic passage space, cessation of labor or placental problems. Parturition is hindered and the temperature of the fetus and the expectant mother increase precipitously. Emergency procedures are required to protect the lives of the fetus and mother. In accordance with the present invention, the occurrence of fetal stress syndome is effectively identified by virtue of the retention of temperature sensing means within the reproductive tract during the period immediately before parturition. After the above-mentioned standard temperature is determined, the rapidly increasing intravaginal temperature is sensed by the sensing means and analyzed, and a signal is delivered to the alarm means to identify the occurrence of the syndrome. Upon such identification, appropriate measures are able to be taken immediately to alleviate the condition.

In addition to the apparatus identified above, the system of the present invention is equipped with other electronic elements as may be appropriate. Thus, the equipment contained within the payload is powered by a miniaturized battery or by a transponder. An antenna is preferably provided when signals are to be relayed to a remote station. Signal amplifiers are suitably integrated, as appropriate. Computer hardware and software are added where necessary for information processing, as well as communication cables, including telephone lines. When the expectant female is located in a large group of animals, and when the alarm is located remotely of the animal, suitable equipment is provided such that the signal transmitted by the relaying means enables the animal to be efficaciously identified.

The following examples illustrate in detail the use of the invention.

EXAMPLE I

In this example, the intravaginal anchor described hereinabove is implanted into the anterior portion of the vagina before the onset of parturition. The anchor is equipped with a temperature sensitive transmitter comprising a temperature sensing means and a relay means. Signals indicative of the sensed temperature are relayed to an a.m. radio receiver and are perceivable by the listener.

Anchors are implanted in six cows, one sow, and seven mares. The following summarizes the experience of each of these animals.

Cow 1910. This is a first-calf heifer. The anchor is expelled as the cow begins contractions and farm personnel are thus signalled as to the onset of parturition. Her labor is very hard and her calf is very large. Assistance is provided and, without it, it is believed that the calf would die and the cow would be in danger.

Cow 1418. Again, the anchor is expelled as the cow begins contractions. A signal is relayed from the temperature sensor to the receiver and alerts farm personnel to the onset of parturition. Suitable assistance is accordingly provided and proves to be important in that the calf is backwards and would die if the parturition was unattended.

Cow 1738. The anchor is expelled as contractions begin and, this time, the dropping of the anchor is visually observed by farm personnel to thus signal the onset of parturition. The cow is carefully monitored during parturition, but labor lasts only 39 minutes and is normal.

Cow 1819. Similar to Cow 1738, the anchor is expelled from this cow as contractions begin. Labor is longer, lasting two hours, twelve minutes, but the parturition is normal.

Cow 1614. Again, the anchor functions flawlessly, being expelled upon the onset of parturition. The temperature drop at expulsion generates a signal that is received on the a.m. radio and assistance is provided. The parturition is normal, except for the occurrence of twins.

Cow 1653. The anchor is expelled as contractions begin. Parturition proceeds quickly and without complications. Sow. This animal labors for two hours 40 minutes and the anchor is expelled moments before the first piglet is born. Ten live piglets and one decomposing piglet are born. If assistance was not rendered, it's expected that three of the piglets would suffocate in placental membranes.

The mares are monitored not only for the onset of parturition but also for the purpose of predicting the onset of parturition in advance of the event. In accordance with the invention, temperature readings are taken each day at 7:30 a.m. Only one of the mares experiences difficulty with the anchor, in that it is gradually expelled twice, before the onset of parturition. This situation is remedied by providing a larger anchor.

Mare 8. After a standard temperature is determined, a temperature increase of 0.2° celsius, in the form of a temperature spike, is sensed. One day thereafter, a temperature decrease of 0.4° celsius is sensed. Twelve hours after the decreased temperature is measured, foaling occurs. The anchor is expelled a few minutes ahead of the foal.

Mare 15. Following the determination of a standard temperature, a temperature increase of 0.5° celsius is sensed. A temperature decrease of 0.8° celsius is then sensed three days later. Foaling follows the decreased temperature measurement by 46 hours, and the anchor is expelled a few minutes ahead of the foal.

Mare 2. After standardization, a temperature increase of 0.3° celsius is sensed and two days later, a temperature decrease of 0.4° celsius is sensed. Foaling follows the decreased temperature measurement by 70 hours, and the anchor is expelled a few minutes ahead of the foal.

Mare 31. After the standard temperature for the animal is determined, a temperature increase of 0.2° celsius is sensed, followed in three days by the sensing of a temperature decrease of 0.5° celsius, which in turn is followed in 28 hours by foaling. The anchor is expelled ten minutes before the appearance of the foal. The foal is unusually large for the mare's size, and without the assistance that is provided, the foal would be in serious jeopardy.

Mare 13. Following standardization, a temperature increase of 0.5° celsius is sensed and a temperature decrease of 0.4° celsius is sensed one day later. Eight hours after the temperature decrease is sensed, foaling is induced successfully. The foal is quite hardy and ready for birth. The anchor is expelled by the placenta as it precedes the foal.

Mare 9. The animal's standard temperature is determined and a temperature increase of 0.4° celsius is then sensed, followed in three days by the sensing of a temperature decrease of 0.9° celsius. Foaling follows the decreased temperature measurement by 140 hours. Labor is very long and hard. The anchor is expelled a few minutes before the foal appears.

Mare 20. A temperature increase of 0.3° celsius is sensed after a standard temperature is determined. A temperature decrease of 0.6° celsius is sensed three days later and foaling follows the decrease by 93 hours. The anchor is expelled a few minutes ahead of the foal.

Summarizing the results of Example I, the anchor is expulsed about 30 minutes ahead of the calf under normal conditions, only a minute ahead of the first piglet, and about 10 minutes ahead of the foal. This timing is excellent in that the parturition alarm summons an attendant at just the right time—not too early and not too late.

EXAMPLE II

An anchor as described hereinabove is provided with a temperature sensing means and a relaying means, both of which are powered by a transponder. The anchor is inserted into the anterior vagina of a mare when the mare is determined to be pregnant. A receiving means is maintained in a farm building, along with a computer capable of analyzing temperature data and detecting alarm conditions.

At 7:30 each morning, the temperature sensing means senses the intravaginal temperature and a signal carrying data indicative of the sensed temperature is passed to the relaying means and transmitted to the receiving means. At the remote station, the signal is received and delivered to the computer. The computer is programmed to compute a standard 7:30 a.m. temperature that is peculiar to the mare by averaging at least three temperature measurements. The relaying means also delivers a signal indicative of the identity of the animal, so that the computer is able to associate the standard temperature to the particular animal.

After the standard temperature has been computed, the temperature sensor continues to collect and deliver data at 7:30 a.m. On the 23rd day following insertion, the sensor senses a temperature rise of 0.2° celsius above the standard, and on the third day following the rise, the sensor senses a temperature drop of 0.4° celsius below the standard. When this data is received by the computer, it is compared to a data base of alarm conditions and recognized as being indicative of a condition predictive of parturition within six and probably within three days. At this point the computer registers the time of the alarm condition and causes a light to flash adjacent to a number identifying the animal on a panel within the farm building. The panel is reviewed at regular intervals by a farm worker and, upon viewing the flashing light, the mare is retrieved from the corral and placed in a maternity stall.

Three days after the mare is placed in the maternity stall, the temperature sensor senses a precipitous intravaginal temperature rise of four degrees over the standard temperature in the course of four hours. Indicative data is delivered to the computer which, again, compares the data to a data base of alarm conditions and recognizes the data as being indicative of fetal stress syndrome. The computer causes a bell to ring that can be heard throughout an area in which at least one farm worker is always present. The farm worker immediately comes to the assistance of the mare, determines that a Caesarean section is appropriate, and the surgery is performed.

EXAMPLE III

An apparatus identical to that described in Example II is placed intravaginally in another mare, and similar temperature measurements are sensed and interpreted by the computer, except that there is no indication of fetal stress syndrome. Instead, three days after the mare is placed in the maternity stall, parturition begins and the anchor is expelled. The temperature sensor senses an abrupt temperature drop of 15° celsius and data indicative of this drop are delivered to the computer. The data are compared by the computer to a data base of alarm conditions and the computer recognizes the data as being indicative of the onset of parturition. At that point, the computer causes the bell, described above, to ring and farm personnel immediately provide assistance to the mare and the foal.

EXAMPLE IV

An intravaginal anchor as described hereinabove is equipped with a temperature sensor and relay means and placed intravaginally into a human patient three weeks before parturition is expected. Signals indicative of temperatures sensed are received by a remote receiver and delivered to a computer. A standard temperature is determined after five days in accordance with the procedures outlined above. A temperature rise of 0.2° celsius is then sensed, followed in two days by a temperature drop of 0.4° celsius. The computer analyzes the deviant temperatures and causes the sounding of a buzzer that is carried by the expectant mother. The mother contacts her physician and makes appropriate preparation for birth within six and probably within three days.

It will be apparent to those skilled in the art that many modifications and variations may be introduced without departing from the inventive scope of the present teachings.

I claim:

1. A system for detecting the onset of parturition by a mammalian female comprising an anchor, a temperature sensing means affixed to said anchor, and an alarm means, wherein said anchor has a diameter that is smaller than an interior diameter of a posterior portion of said female's vagina at the onset of parturition but greater than said interior diameter prior to the onset of parturition, and smaller than an interior diameter of an anterior portion of said female's vagina before and at the onset of parturition, such diameters being a function of muscular activity, such that said anchor is retained in said anterior portion for a period prior to the onset of parturition and expulsed at the onset of parturition, and wherein said sensing means senses a temperature differential at the location of said anchor before and after expulsion and actuates said alarm means.

2. The system of claim 1 wherein said anchor comprises an elongated tubular body and a flanged area, said diameter of said anchor being located at said flanged area.

3. The system of claim 2, wherein said flanged area is provided with a plurality of slots disposed substantially parallel to each other and to the length of said body such that, in an expanded position, the ends of said body are moved towards each other and flange portions of said body between adjacent pairs of said slots are distended away from an axis of said body to define said diameter of said anchor and, in a collapsed position, the ends of said body are moved away from each other and said flange portions are retracted towards said axis, and wherein said anchor further comprises a biasing means for urging said body into said expanded position.

4. The system of claim 1 wherein said alarm means is affixed to said anchor.

5. The system of claim 1 wherein said alarm means is located at a remote station and said system further comprises a relaying means affixed to said anchor and a receiving means located at said station, such that said sensing means actuates said alarm means by generating a signal that is relayed by said relaying means, received by said receiving means and delivered to said alarm means.

6. The system of claim 1 further comprising a temperature analyzing means that analyzes signals generated by said sensing means and generates signals that actuate said alarm means.

7. A method for detecting the onset of parturition by a mammalian female comprising the steps of:
providing a system for detecting the onset of parturition by a mammalian female comprising an anchor, a temperature sensing means affixed to said anchor, and an alarm means, wherein said anchor has a diameter that is smaller than an interior diameter of a posterior portion of said female's vagina at the onset of parturition but greater than said interior diameter prior to the onset of parturition, and smaller than an interior diameter of an anterior portion of said female's vagina before and at the onset of parturition, such diameters being a function of muscular activity, such that said anchor is retained in said anterior portion for a period prior to the onset of parturition and expulsed at the onset of parturition, and wherein said sensing means senses a temperature differential at the location of said anchor before and after expulsion and actuates said alarm means;
inserting said anchor into said anterior portion of the vagina of said female prior to the onset of parturition;
causing said anchor to be expelled from said vagina at the onset of parturition by contractions of the vaginal musculature; and
actuating said alarm when said anchor is expelled.

8. A method for predicting the onset of parturition in a mammalian female comprising the steps of measuring the intravaginal temperature of said female for a plurality of days at the same time of day for each of said days, averaging said temperatures to determine a standard intravaginal temperature for said female for said time, and subsequently measuring an intravaginal temperature for said female for said time that is at least about 0.4° celsius lower than said standard temperature, such that the onset of parturition is predicted by said subsequent measurement.

9. The method of claim 8 wherein the attainment of fetal readiness is determined at the same time that said subsequent measurement is made.

10. The method of claim 8 wherein the onset of parturition occurs within six days of said subsequent measurement.

11. The method of claim 10 wherein the onset of parturition occurs less than three days after said subsequent measurement.

12. The method of claim 8 wherein the onset of parturition is further predicted by measuring, after determining said standard intravaginal temperature but before measuring said lower temperature, an intravaginal temperature for said female for said time that is at least about 0.2° celsius higher than said standard temperature.

13. The method of claim 8 wherein said lower temperature is in the range of about 0.4° to 1.0° celsius.

14. The method of claim 8 wherein said plurality of days is about five days.

15. The method of claim 12 wherein said higher temperature is in the range of about 0.2° to 0.5° celsius.

16. The method of claim 12 wherein said higher temperature precedes said temperature by not more than about three days.

17. The method of claim 8 further comprising the step of first inserting an intravaginal device into the vagina of said female, wherein said device comprises an anchoring means for retaining said device within said vagina, a temperature sensing means, and a relaying means, wherein said temperatures are sensed by said sensing means and relayed to a remote station.

18. A method for the inducement of parturition comprising the steps of determining the attainment of fetal readiness in accordance with the method of claim 9 and subsequently inducing said parturition.

19. A method for performing Caesarean section comprising the steps of determining the attainment of fetal readiness in accordance with the method of claim 9 and subsequently performing said Caesarean section.

20. The method of claim 8 wherein said female is selected from the human species or the bovine, ovine, caprine equine or porcine families.

21. The method of claim 20 wherein said female is selected from the equine family.

22. A method for detecting the occurrence of fetal stress syndrome in a mammalian female immediately before parturition comprising the steps of measuring the intravaginal temperature of said female for a plurality of days at the same time for each day, averaging said temperatures to determine a standard intravaginal temperature for said female for said time and, subseqently, measuring a rapidly increasing intravaginal temperature, such that the occurrence of fetal stress syndrome is detected by said subsequent measurement.

23. The method of claim 22 wherein said plurality of days is about five days.

* * * * *